United States Patent
Tam

[19]

[11] Patent Number: 5,805,659
[45] Date of Patent: Sep. 8, 1998

[54] METHOD AND APPARATUS FOR SPIRAL SCAN REGION OF INTEREST IMAGING

[75] Inventor: Kwok C. Tam, Edison, N.J.

[73] Assignee: Siemens Corporate Research, Inc., Princeton, N.J.

[21] Appl. No.: 724,697

[22] Filed: Sep. 30, 1996

[51] Int. Cl.$^6$ .................................................. A61B 6/03
[52] U.S. Cl. ........................................... 378/15; 378/901
[58] Field of Search ...................................... 378/15, 901

[56] References Cited

U.S. PATENT DOCUMENTS

| | | | |
|---|---|---|---|
| 5,257,183 | 10/1993 | Tam | 364/413.19 |
| 5,383,119 | 1/1995 | Tam | 364/413.19 |
| 5,404,293 | 4/1995 | Weng et al. | 378/15 |
| 5,446,776 | 8/1995 | Tam | 378/4 |
| 5,463,666 | 10/1995 | Eberhard et al. | 378/4 |
| 5,504,792 | 4/1996 | Tam | 378/15 |
| 5,625,660 | 4/1997 | Tuy | 378/15 |

*Primary Examiner*—David P. Porta
*Assistant Examiner*—David Vernon Bruce
*Attorney, Agent, or Firm*—Lawrence C. Edelman

[57] ABSTRACT

A scanning and data acquisition method and apparatus for three-dimensional computerized tomographic imaging of a region of interest (ROI) of an object which is smaller than the object itself and having upper and lower boundaries which are completely within a field of view of an imaging system comprises merely a continuation of the scan trajectory used for scanning the main portion of the ROI so as to extend past its upper and lower boundaries. In a preferred embodiment, the scan path of the present invention consists of a main spiral scan path comprising a plurality of spiral turns, or stages, for scanning between upper and lower boundaries of the ROI, and at least a portion of an extra single spiral turn of the scan path at each end thereof. For image reconstruction, cone beam data for source positions corresponding to circular portions of the scan are approximated in the present invention by interpolation of data acquired from source positions on the extra spiral turn with data acquired from that turn of the main spiral scan that is adjacent thereto.

17 Claims, 3 Drawing Sheets

CIRCULAR ARC SCAN PATH

X-RAY SOURCE

METHOD AND APPARATUS FOR SPIRAL SCAN REGION OF INTEREST IMAGING

BACKGROUND OF THE INVENTION

1. Field of the Invention

The present invention relates generally to computerized tomography (CT), and more specifically, to a scan path for three-dimensional (3D) CT imaging of a region of interest.

2. Description of the Background Art

In conventional (third generation) computerized tomography (CT) for both medical and industrial applications, an x-ray fan beam and a linear array detector are used to achieve two-dimensional (2D) imaging. While the acquired data set may be complete and image quality correspondingly high, only a single slice of an object is imaged at a time. When a 3D image is required, an approach which acquires a stack of slices is employed. Acquiring a 3D data set one 2D slice at a time is inherently slow. Moreover, in medical applications, motion artifacts occur because adjacent slices are not imaged simultaneously. Also, dose utilization is less than optimal because the distance between slices is typically less than the x-ray collimator aperture, resulting in double exposure to many parts of the body. In 2D CT, the scanning path of the source is often simply a circular scan about the object. A linear array detector is fixed relative to the source. In fourth generation CT devices, such as an electron beam CT scanner manufactured and available from Imatron, Inc. of California, however, the source of the x-rays rotates (due to magnetic deflection) and the detector array is stationary.

In a system employing true cone beam geometry for 3D imaging, a cone beam x-ray source and a 2D area detector are used. An object is scanned, preferably over a 360° angular range, either by moving the x-ray source in a scanning circle about the object or by rotating the object while the source remains stationary. In either case, the area detector is fixed relative to the source. Relative movement between the source and object which is to be imaged provides scanning of the object. Compared to the conventional 2D stack of slices approach to achieve 3D imaging, cone beam geometry has the potential to achieve 3D imaging of both medical and industrial objects both rapidly and with improved dose utilization.

In order to provide a complete set of projection data for accurate 2D or 3D imaging of an object (or a region of interest in an object), it is necessary to satisfy completeness criteria. These criteria are well known, and are described in detail, for example, by Smith, B. D., in the publication "Image Reconstruction From Cone-Beam Projections, Necessary and Sufficient Conditions and Reconstruction Methods", IEEE Transactions Medical Imaging, MI-4 (1985), pp. 14–25. Basically, what is required is that any plane passing through the object or region of interest must intersect the scan path at one or more locations. The completeness criteria are also discussed in my earlier issued U.S. Pat. No. 5,383,119 entitled METHOD AND APPARATUS FOR ACQUIRING COMPLETE RADON DATA FOR EXACTLY RECONSTRUCTING A THREE-DIMENSIONAL COMPUTERIZED TOMOGRAPHY IMAGE OF A PORTION OF AN OBJECT RADIATED BY A CONE BEAM SOURCE issued on Jan. 17, 1995, hereby incorporated by reference. Additionally, this patent notes that the acquired data set is complete only if it provides data at every point in the Radon space, i.e., the Radon space must be sufficiently filled with data over the so-called "region of support" which topologically corresponds to the field of view occupied by the region of interest of the object in real space. Radon data is typically acquired by exposing the entire object within the field of view to the source.

As described in my fore-noted U.S. Pat. No. 5,383,119, 3D image reconstruction techniques have difficulties imaging objects and regions which have a rather long, wide or tall dimension. If the height, width or length of an object or region of interest is great, it is often impractical or difficult to obtain a detector array with sufficient height or width to obtain projection data from the object or region of interest. Generally, the detector must have a height and width at least somewhat greater than the height and width of the object or region of interest, otherwise, some x-ray data would be missing. Also, since some of the x-rays have passed through portions of the object which are not in the region of interest (where the region of interest is only part of the object), the cone beam data collected would not exclusively represent data from such a region of interest and therefore lead to image blurring and the generation of image artifacts.

Sufficient filling of the Radon space by apparatus having various scanning trajectories (paths) and using an area detector which is smaller than the region of interest being imaged are known for performing an exact image reconstruction. For example, in the above-noted U.S. Pat. No. 5,383,119, a rather complex technique is described for manipulating the acquired cone beam data so as to discard and recover data, as appropriate, so that that only cone beam data directly attributable to the region of interest is used for image reconstruction. In my earlier issued U.S. Pat. No. 5,463,666 entitled HELICAL AND CIRCLE SCAN REGION OF INTEREST COMPUTERIZED TOMOGRAPHY issued Oct. 31, 1995, hereby incorporated by reference, a cone beam CT system is disclosed in which a region of interest portion of an object can be imaged without blurring or artifact introduction from imaging portions of the object not within the region of interest. A controllably movable source and relatively small area detector are controlled so as to define a scan path, or trajectory, consisting of a central spiral portion having one circle portion at each end of the spiral portion which is level with upper and lower boundaries of the region of interest. The switch from a spiral path to a circular path is necessary in order to obtain complete cone beam data at the upper and lower boundaries of the region of interest without blurring caused by imaging portions of the object that are outside the region of interest, as described in greater detail in my fore-noted U.S. Pat. No. 5,463,666.

Although the above and other techniques have been useful, they require scan paths which have abrupt shifts in movement. Since the object being imaged may be a patient, such abrupt shifts in scan movement are undesirable if the patient must be moved for the scanning. Even if the patient is stationary and it is the source that is moved to obtain an abrupt shift, this is also less than desirable due to the extra mechanical stress it places on the imaging system.

It would be desirable to provide a CT imaging method and apparatus in which a region of interest can be scanned without the need for providing different scan configurations for scanning the region of interest, and more specifically without the need to suddenly change the scan path movement or trajectory used for imaging the central portion of the region of interest so as to provide circular scan paths at the upper and lower boundaries of the region of interest.

SUMMARY OF THE INVENTION

In accordance with the principles of the present invention, the abrupt transition of the scan path from one trajectory for scanning the main portion of a region of interest of an object to a different trajectory for scanning its upper and lower boundaries, is avoided by replacing the different, circular, scan trajectories of the scan path required by the prior art with merely a continuation of the scan trajectory used for scanning the main portion of the ROI so as to extend past its upper and lower boundaries. In a preferred embodiment, the scan path of the present invention consists of a main spiral scan path comprising a plurality of spiral turns, or stages, for scanning between upper and lower boundaries of a region of interest in an object, and at least a portion of an extra single spiral turn of the scan path at each end thereof. For image reconstruction, cone beam data for source positions which in the prior art were on the circular portion of the scan, are approximated in the present invention by interpolation of data acquired from source positions on the extra spiral turn with data acquired from that turn of the main spiral scan that is adjacent thereto.

DETAILED DESCRIPTION OF THE INVENTION

Figure 1:
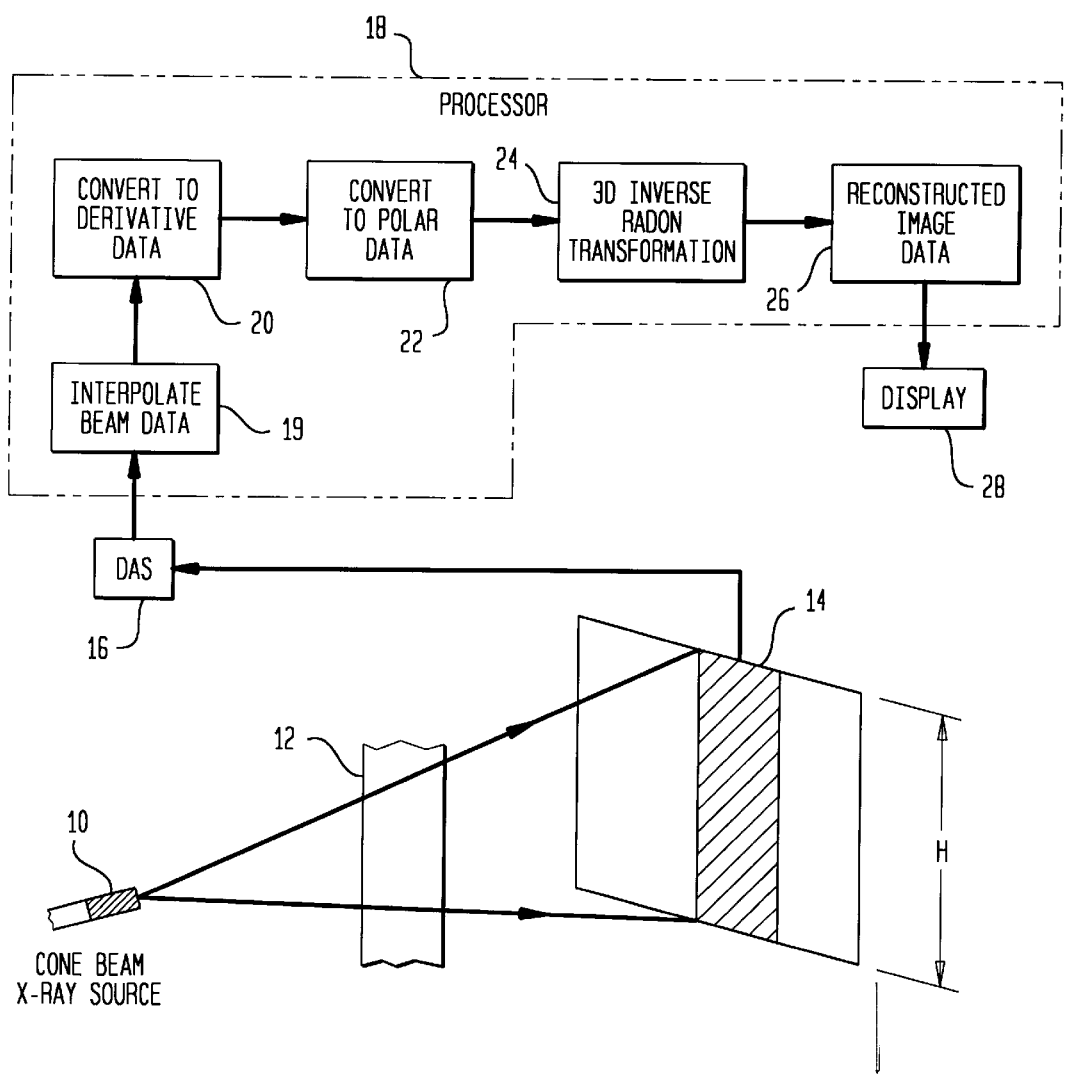
FIG. 1 is a simplified perspective illustration of the imaging of an object using an x-ray source and detector, combined with a simplified block diagram of image reconstruction according to the present invention.

As shown in FIG. 1 a cone beam x-ray source 10 generates cone beam energy which passes through and about a region of interest of an object 12 which is to be imaged. Although source 10 is shown as a cone beam x-ray source, other types of beam sources, such as a fan beam and other types of imaging energy might be used, such as neutrons, positrons, etc. The imaging energy, of whatever type used, is detected by detector 14. Although individual detector elements are not shown, it will be readily understood that detector 14 is a two-dimensional array of individual detector elements. Relative movement between the source 10 and object 12 is used to provide complete cone beam data about object 12. For example, object 12 could be moved to cause scanning as discussed in detail below. Alternately, and equivalently, source 10 and detector 14 could be moved in such a scan path. The object may be a work piece or a medical patient or other item for imaging.

Signals corresponding to the sensed x-ray energy falling on elements within detector 14 are supplied to a data acquisition system (DAS) 16 which, like the previously described portions of FIG. 1, may operate in a fashion well known to those of ordinary skill in this technology.

Cone beam data from the data acquisition system 16 is supplied to a processor 18, which may be a computer programmed to perform various data conversions illustrated by the blocks within the processor 18. Block 19, which is a key feature of the present invention, interpolates projection or cone beam data that spans upper and lower boundaries of the region of interest. As will be discussed in detail below, the interpolated data corresponds to cone beam data obtained by the circular scan paths of my fore-noted prior U.S. Pat. No. 5,463,666. Next, at block 20, the cone beam data is converted to Radon derivative data. This may be accomplished using the techniques described in U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993, hereby incorporated by reference. The Radon derivative data is then converted to Radon data at polar grid points at block 22 using, for example, a technique described in U.S. Pat. No. 5,446,776 entitled TOMOGRAPHY WITH GENERATION OF RADON DATA ON POLAR GRID POINTS issued Aug. 8, 1995, hereby incorporated by reference. The Radon data at the polar grid points is supplied to block 24 which performs an inverse 3D Radon transformation using well known techniques, such as those described in detail in the fore-noted U.S. Pat. No. 5,257,183.

At block 26 reconstructed image data is developed, and then fed from processor 18 to a display 28, which may operate in known fashion, to provide 3D CT imaging of the object 12 or the region of interest portion (not separately shown in FIG. 1).

A more detailed description of the blocks of FIG. 1, other than block 19, can be found in the patents incorporated by reference herein.

Figure 2:
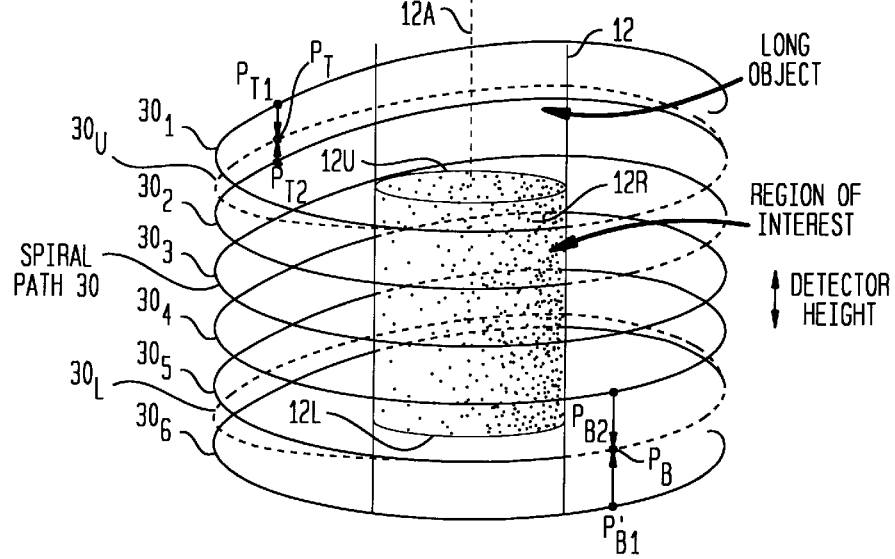
FIG. 2 shows a simplified perspective illustration of a region of interest of an object and a scan path in accordance with the invention for scanning around it.

Turning now to FIG. 2, the object 12 is shown as including a region of interest 12R, the length of which is less than the length of object 12. A spiral scan path 30 is illustrated that surrounds object 12 with a plurality of turns or stages represented by $30_1$, $30_2$, $30_3$, $30_4$, $30_5$, $30_6$ and completely span object 12 from a point below a lower boundary 12L of the region of interest 12R to a point above an upper boundary 12U of the region of interest 12R. The top turn $30_1$, bottom turn $30_6$, and the various turns of spiral path 30 therebetween collectively define a cylinder centered about axis 12A, which is an axis of symmetry of the region of interest 12R.

As known by the prior art (U.S. Pat. No. 5,463,666), two circular scan paths (shown by dashed lines 30U and 30L in FIG. 1) level with upper and lower boundaries 12U and 12L, respectively, are required for accurately reconstructing an image from a region of interest that is smaller than the object being scanned. As in the present invention, in the prior art the main spiral portion of the scan path is implemented by translation of the object while the x-ray source scans in a circular motion, whereas for implementation of the upper and lower circular portions of the scan path, no translation motion on the part of the object was provided. However, in the prior art the sudden start and stop of the object translation motion between the circular portions of the scan path and the spiral portion may cause difficulty in some imaging systems. This difficulty may relate to both image degradation, as well as mechanical and structural problems. In the case of a medical scanning system, the patient table may have to undergo abrupt starts and abrupt stops, respectively, at the two transitions. For the reasons noted above, these abrupt starts and stops are undesirable and should be avoided.

Since in the present invention the spiral scan path is continuous throughout the region of interest, from below level 12L to above level 12U, abrupt changes in the scan path of the prior art are avoided.

In accordance with a first embodiment of the present invention, scan path turns $30_1$–$30_6$ are mutually spaced by a distance H, which corresponds to the height of detector 14 in FIG. 1. This will allow the detector 14 to assemble a complete set of cone beam or projection data relative to the region 12R without any overlap.

The path 30 corresponds to the desired movement of the source 10 about the object 12 for providing exact image reconstruction in accordance with the forenoted U.S. Pat. No. 5,463,666, it being understood that the detector 14 (FIG. 1 only) would be maintained in a fixed position relative to the source 10. Instead of scanning the source 10 and detector 14 about the object 12 in the path or trajectory 30 shown in FIG. 2, one could equivalently rotate and move object 12 to produce the illustrated scan path. In that case, the scan path would illustrate the apparent movement of the source with respect to a frame of reference fixed to the object 12.

In accordance with the principles of the present invention, the cone beam data obtained in the prior art as a result of the upper and lower circular scans 30U and 30L are obtained by interpolation of the cone beam data obtained from scan portions that are adjacent to the upper and lower boundaries 12U and 12L of object 12. More specifically, cone beam data obtained for source positions on turns $30_1$ and $30_2$ are interpolated, as well as cone beam data obtained for source positions on turns $30_5$ and $30_6$, so as to effectively obtain cone beam data from source positions on circular scans 30U and 30L. An example of such interpolation is shown in FIG. 2, wherein for a source position $P_T$ level with upper boundary 12U, cone beam data obtained from source position $P_{T1}$ from turn $30_1$ is averaged with cone beam data obtained from source position $P_{T2}$ from turn $30_2$. The averaging is carried out with a weighting of the cone beam data in direct proportion to the closeness of the actual source positions $P_{T1}$ and $P_{T2}$ to the desired position $P_T$, i.e., the closer the actual source position to the desired source postion, the greater the weight given to the cone beam data obtained. Similar interpolation is carried out for source positions on turns $30_5$ and $30_6$. Once the interpolated cone beam data is obtained, it is combined with the remainder of the cone beam data obtained from those scans intermediate the upper and lower boundaries 12U and 12L of object 12R, for reconstruction an image in the manner previoulsy described.

Figure 5:
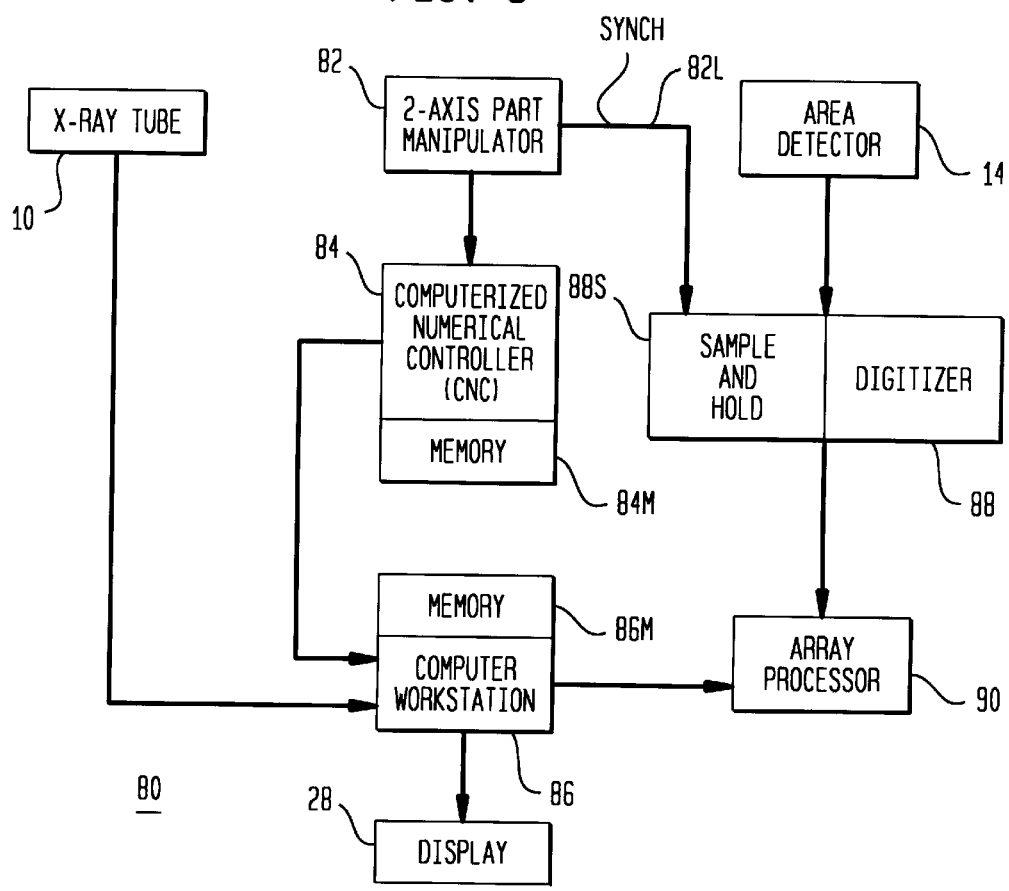
FIG. 5 illustrates a simplified block diagram of apparatus operating in accordance with the present invention.

Turning now to FIG. 5, a system 80 according to the present invention will be discussed. The system includes the source 10 and area detector 14. Although the source 10 has been shown as an x-ray tube, the cone beam source 10 has been shown as an x-ray tube, the cone beam source 10 could alternately provide neutrons, positrons, or other forms of radiation or electron magnetic energy from a point source. Alternately, other forms of imaging energy might be used.

A manipulator 82, which may be a two-axis part manipulator, is used to provide the relative scanning movement between the object (not shown in FIG. 6) which is used to be imaged and the source 10. Although manipulator 82 is designed to move the object, the manipulator 82 might alternately move the source 10.

The manipulator 82 is controlled by a known computerized numerical controller 84, which may, for example, be of a type made by Aerotech. The controller 84 may include a memory 84M having data defining various scan paths in known fashion. Alternately, and also using well known techniques, a memory 86M of a computer work station 86, which is connected to the controller 84, may have the data which defines movements of the manipulator 82 and therefore defines the scan path or trajectory. In either case, the defined scan paths would be the two parallel circles with spiral turns interconnecting them as discussed in detail above. The computer work station 86 (which may include the processor 18 of FIG. 1) may be a work station made by Sun, although other computer work stations and possibly even personal computers might be used in place of the work station. The computer work station controls the other components of the system 80 in known fashion.

Connected to the area detector 14 is a digitizer 88 which operates in known fashion to convert analog signals from the area detector into digital signals representative of the image of the object under test. The digitizer 88 may include sample and hold circuits 88S operating in response to a synch signal on line 82L in known fashion.

The digitized values corresponding to the sense radiation from the detector elements within detector 14 are supplied by the digitizer 88 to a data array processor 90. The array processor 90, which may be of a known commercially available type such as a Meiko M40, provides the necessary signal processing for the signals coming from the digitizer 88, the array processor 90 (which may include or be the processor 18 of FIG. 1) may perform the necessary image reconstruction and processing such that a display might be connected directly to the array processor to display the images from the CT scan. However, in the arrangement shown in FIG. 5, the image data from array processor 90 is supplied to computer work station 86 and the computer work station 86 in turn supplies the data with or without further processing, to the display 28 which displays the CT images. The computer 86 or, more preferably, array processor 90 reconstructs an image from the projection data.

Thus, there has been shown and described a novel scan path for 3D CT imaging which satisfies all the objects and advantages sought. Many changes, modifications, variations and other uses and applications of the subject invention will, however, become apparent to those skilled in the art after considering this specification and its accompanying drawings, which disclose preferred embodiments thereof. For example, although in the illustrated preferred embodiment of the apparatus shown in FIG. 2 scan path 30 has stages or turns with a constant spacing therebetween, for improving the interpolation accuracy, it would be desirable that the spacing between the turns adjacent the upper and lower boundaries have a smaller pitch, i.e., be spaced closer together. Thus, if the pitch of the main spiral is relatively large, the pitch size of the additional spiral turns should be reduced to achieve the desired interpolation accuracy. The reduced pitch size is achieved by translating the patient table at reduced speed. In accordance with a further aspect of the invention, to further improve the interpolation accuracy, the pitch of the first and the last turn of the main spiral should also be reduced. In this alternative embodiment, the translation speed of the patient table changes in the following manner:

1. Ramping up from rest during the first two rotations of the x-ray source; the first rotation corresponds to the first additional spiral turn, and the second rotation to the first turn of the main spiral.
2. Maintaining the same speed until the last two rotations of the x-ray source.
3. Ramping down to rest during the last two rotations of the x-ray source; the last rotation corresponds to the last additional spiral turn, and the second last rotation to the last turn of the main spiral.

Figure 3:
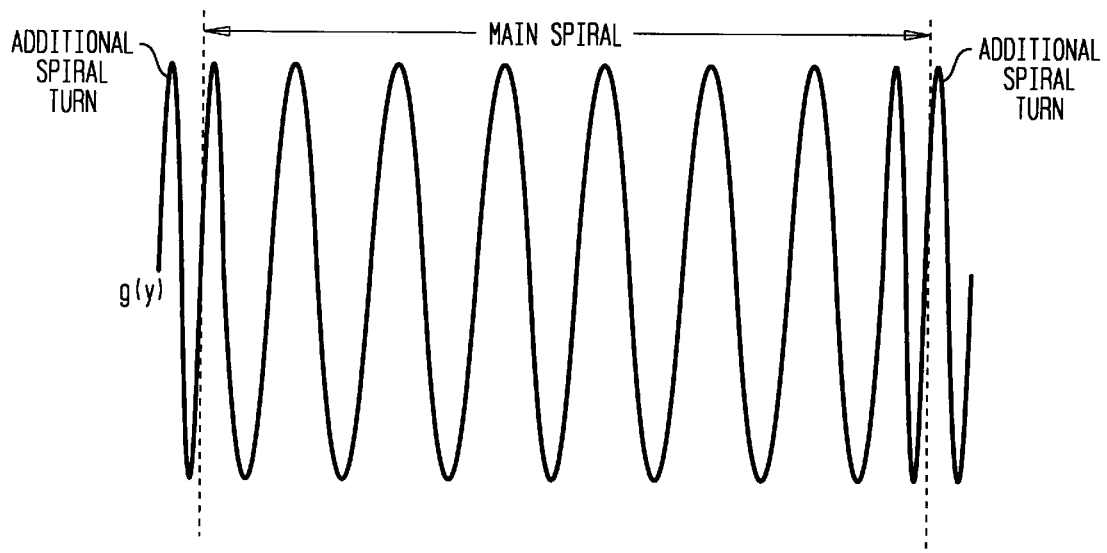
FIG. 3 illustrates an alternative embodiment of the scan path of the present invention.

The profile of the complete spiral scan is illustrated in FIG. 3.

Figure 4:
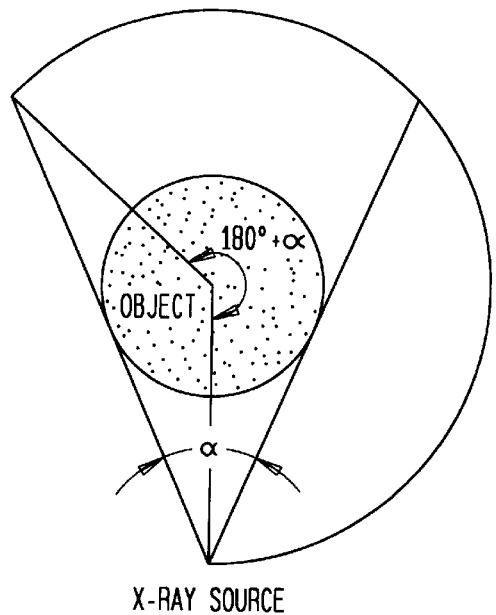
FIG. 4 illustrates a further alternative embodiment of the scan path configuration of the present invention.

In the above discussion it is assumed that the two circle scans $30_U$ and $30_L$ in FIG. 2 are complete circles. In fact they do not need to be complete circles, they only need to be a major circular arcs of angular range at least (180°+α), where α is the fan angle. This is illustrated in FIG. 4. It can be shown that this angular range suffices to provide complete cone beam data to reconstruct the region-of-interest. Similarly, the additional spiral turns $30_1$ and $30_6$ illustrated in FIG. 2 to replace the two circle scans only need to cover an angular range of at least (180°+α).

All such changes, modifications, variations and other uses and applications which do not depart from the invention as described and claimed herein are deemed to be covered by this patent, which is limited only by the claims which follow as interpreted in light of the foregoing description.

I claim:

1. A scanning and data acquisition method for three-dimensional computerized tomographic imaging of a region of interest of an object which is smaller than the object itself and having upper and lower boundaries which are completely within a field of view of an imaging system and radially centered on a predetermined axis, the method comprising the steps of:

applying cone beam energy from a cone beam source to at least a portion of the object;

defining a source scanning trajectory as a path traversed by the source;

using the cone beam source and an area detector with at least the source movably positioned relative to the object, for scanning about the region of interest of the object;

specifying a source scanning trajectory for completely obtaining Radon data for accurately reconstructing a 3D CT image of the region of interest of the object as comprising only a spiral scan defining a plurality of spaced stages on a predetermined geometric surface surrounding the region of interest, such that each plane passing through the region of interest intersects the scanning trajectory in at least one point, the area detector having a predetermined dimension extending sufficiently along a direction generally parallel to the predetermined axis to span at least two consecutive stages having the largest spacing therebetween;

scanning at a plurality of positions along the source scan trajectory to obtain cone beam projection data corresponding to respective portions of the region of interest; and processing the cone beam projection data corresponding to energy which passed through the object, to provide a data set which can be reconstructed into an image of the region of interest of the object.

2. The method of claim 1, wherein said specifying step specifies as said source scanning trajectory a spiral scan path having a higher pitch at opposite ends of the region of interest, and a uniform pitch therebetween.

3. The method in accordance with claim 1, wherein the processing step includes performing an interpolation of the cone beam projection data from a plurality of source positions along adjacent stages of said scan path that span the upper and lower boundaries of the region of interest.

4. The method in accordance with claim 3, wherein said interpolation is carried out with a weighting of the cone beam data in direct proportion to the closeness of actual source positions of the adjacent stages to desired source positions on the upper and lower boundaries of the region of interest.

5. The method of claim 1, wherein said specifying step specifies as said source scanning trajectory a spiral scan path having a higher pitch for the stages that span the upper and lower boundaries of the region of interest, and a uniform, lower pitch, for stages that span the region of interest therebetween.

6. The method of claim 3, wherein said processing step further comprises determining cone beam data for each of a plurality of source positions along said source scanning trajectory, computing Radon derivative data from said cone beam data, processing said derivative data to generate 3D inverse Radon transform data, and reconstructing image data from said inverse Radon transform data.

7. The method of claim 6, including the further step of displaying a 3D image using said image data.

8. A scanning and data acquisition imaging apparatus for three-dimensional computerized tomographic imaging of a region of interest of an object which is smaller than the object itself and having upper and lower boundaries which are completely within a field of view of the imaging apparatus and radially centered on a predetermined axis, the apparatus comprising:

a cone beam source for applying cone beam energy to at least a portion of the object;

an energy detector positioned for receiving cone beam energy that had been applied to said object by said cone beam source;

a scanning device for causing relative motion, scanning, between the cone beam source and the object such that the cone beam source moves along a source scanning trajectory relative to the object, while maintaining the energy detector in a position to receive energy that had been applied to said object;

trajectory defining means operatively coupled to the scanning device for determining a source scanning trajectory for scanning by said cone beam source about the object, said source scanning trajectory comprising only a spiral scan path for obtaining complete Radon data for accurately reconstructing a 3D CT image of the region of interest of the object, said spiral scan path comprising a plurality of spaced stages on a predetermined geometric surface spanning the region of interest of the object so as to extend past its upper and lower boundaries, such that each plane passing through the region of interest intersects the source scanning trajectory in at least one point, the area detector having a predetermined dimension extending sufficiently along a direction generally parallel to the predetermined axis to span at least two consecutive stages having the largest spacing therebetween;

means for acquiring cone beam projection data from said detector at a plurality of source positions along the source scanning trajectory so as to obtain cone beam projection data corresponding to respective portions of the region of interest; and processing means for processing the cone beam projection data corresponding to energy which passed through the object, to provide a data set which can be reconstructed into an image of the region of interest of the object.

9. Apparatus in accordance with claim 8, wherein said trajectory defining means defines as said source scanning trajectory a spiral scan path having a higher pitch at opposite ends of the region of interest, and a uniform pitch therebetween.

10. Apparatus in accordance with claim 8, wherein said trajectory defining means defines as said source scanning trajectory a spiral scan path having a higher pitch for the stages that span the upper and lower boundaries of the region of interest, and a uniform, lower pitch, for stages that span the region of interest therebetween.

11. Apparatus in accordance with claim 8, wherein said processing means performs an interpolation of the cone beam projection data from a plurality of source positions along adjacent stages of said scan path that span the upper and lower boundaries of the region of interest.

12. Apparatus in accordance with claim 11, wherein said processing means performs said interpolation with a weighting of the cone beam projection data in direct proportion to the closeness of the actual source positions of the adjacent stages to the desired source position on the upper and lower boundaries of the region of interest.

13. Apparatus in accordance with claim 8, wherein said processing means comprises means for determining cone beam data for each of a plurality of source positions along said source scanning trajectory, means for computing Radon derivative data from said cone beam data, means for processing said derivative data to generate 3D inverse Radon transform data, and means for reconstructing image data from said inverse Radon transform data.

14. Apparatus in accordance with claim 13, further including display means for displaying a 3D image using said image data.

15. Apparatus in accordance with claim 8, wherein said scanning device comprises a two-axis part manipulator connected to the source and the detector to achieve the relative motion between the cone beam source and the object while object remains stationary.

16. Apparatus in accordance with claim 8, wherein said scanning device comprises a two-axis part manipulator connected to the object to achieve the relative motion between the cone beam source and the object while the source and the detector remain stationary.

17. Apparatus in accordance with claim 8, wherein said scanning device translates the object while rotating the source and detector to achieve spiral relative movement of the source with respect to the object.

* * * * *